US00PP31421P2

(12) United States Plant Patent
Hansen

(10) Patent No.: US PP31,421 P2
(45) Date of Patent: Jan. 28, 2020

(54) ***AGAPANTHUS* PLANT NAMED 'GALAXY BLUE'**

(50) Latin Name: ***Agapanthus praecox* (L.) hybrid**
Varietal Denomination: Galaxy Blue

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/350,792

(22) Filed: Jan. 14, 2019

(51) Int. Cl.
*A01H 5/02* (2018.01)
*A01H 6/04* (2018.01)

(52) U.S. Cl.
USPC ..... Plt./398

(58) Field of Classification Search
USPC ..... Plt./263.1, 398
See application file for complete search history.

*Primary Examiner* — Susan McCormick Ewoldt
*Assistant Examiner* — Karen M Redden

(57) ABSTRACT

A new and distinct *Agapanthus* plant named 'Galaxy Blue' characterized by winter-hardy compact habit with clean, lanceolate, medium-green foliage that goes dormant in the winter; single dark-blue flowers on medium-tall dark purple scapes flowering beginning about mid-July and with repeating new scapes into mid-September for about eight weeks.

1 Drawing Sheet

Botanical classification: *Agapanthus praecox* (L.) hybrid.
Variety denomination: 'Galaxy Blue'.

STATEMENT REGARDING PRIOR DISCLOSURES UNDER 37 CFR 1.77(B)(6)

The first public disclosure of the claimed plant, in the form of a website to the public and email release to customers, was made by Walters Gardens, Inc. on Feb. 1, 2018. Walters Gardens, Inc. obtained the new plant and information about the new plant directly from the inventor. No plants of *Agapanthus* 'Galaxy Blue' have been sold, in this country or anywhere in the world, nor has any disclosure of the new plant been made, more than one year prior the filing date of this application, and such sale or disclosure within one year was either derived directly or indirectly from the inventor.

BACKGROUND AND ORIGIN OF THE PLANT

The present invention relates to a new and distinct Lily of the Nile plant, *Agapanthus* 'Galaxy Blue' hereinafter also referred to as the new plant or just the cultivar name, 'Galaxy Blue'. *Agapanthus* 'Galaxy Blue' was selected by the inventor in July of 2012 in a trial field at a wholesale perennial nursery in Zeeland, Mich., USA. The new plant originated from a breeding program conducted by the inventor with the specific intention to improve the garden worthiness, expand color regimens and increase flowering period which were some of the criteria of further trials in the trial beds at the same nursery in Zeeland, Mich. The female or seed parent was *Agapanthus campanulatus* subspecies *patens* 'Mooreanus' (not patented) and the male or pollen parent was 'Prolific Blue' (not patented) crossed on Jul. 12, 2010. The new plant was selected as a single seedling from this cross and after confidential evaluations in a trial bed beginning in 2012 in Zeeland, Mich. and was assigned the breeder code H10-07-02 through the remaining trial period.

The new plant has been asexually propagated by division and shoot tip tissue culture at the same wholesale nursery in Zeeland, Mich. since 2012 with all resultant asexually propagated plants having retained all the same unique traits as the original plant. *Agapanthus* 'Galaxy Blue' has proven to be stable and reproduces true to type in successive generations of asexual reproduction.

The most similar known lily of the Nile cultivars are: the female parent 'Mooreanus' has lighter blue flowers on much shorter stems that lack the dark purple coloration. 'Stevie's Wonder' (not patented), 'Ellamae' U.S. Plant Pat. No. 7,297, and 'Elaine' U.S. Plant Pat. No. 7,303. 'Navy Blue' (not patented) has flowers that are a darker purple hue on slightly shorter stems. 'Stevie's Wonder' has flowers in larger heads that are darker blue-violet on taller stems and has wider foliage. 'Elaine' has taller stems of darker violet-blue flowers. 'Ellamae' has slightly shorter stems of darker violet blue. 'Stevie's Wonder', 'Elaine' and 'Ellamae' have not been shown to be as hardy as 'Galaxy Blue'. 'Blue Yonder' (not patented) lacks the dark purple peduncle color. 'Blue Globe' (not patented) has shorter flower stems and lacks the dark purple peduncle color. 'Bressingham Blue' (not patented) has shorter flower stems without the dark purple coloration and thinner, more wiry and less upright. 'Prolific Blue' has less purple pigment on the stems and the flowers nod more. Compared with 'Blue Flare' U.S. Plant Pat. No. 26,422 the new plant has deeper blue colored flowers, longer blooming period, and is more winter hardy.

*Agapanthus* 'Galaxy Blue' differs from all other lily of the Nile plants known to the applicant, by the combination of the following traits:

1. Dark blue flowers;
2. Dark purplish stems with pigment concentrated toward flowers;
3. Long season of bloom.
4. Winter-hardy to USDA zone 6, compact, clean, medium-green foliage that goes dormant in the winter;

5. Flowering begins about mid-July with excellent coverage and sending new scapes into mid-September for about eight weeks;

BRIEF DESCRIPTION OF THE DRAWINGS

The photograph of the new plant demonstrates the overall appearance of the plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
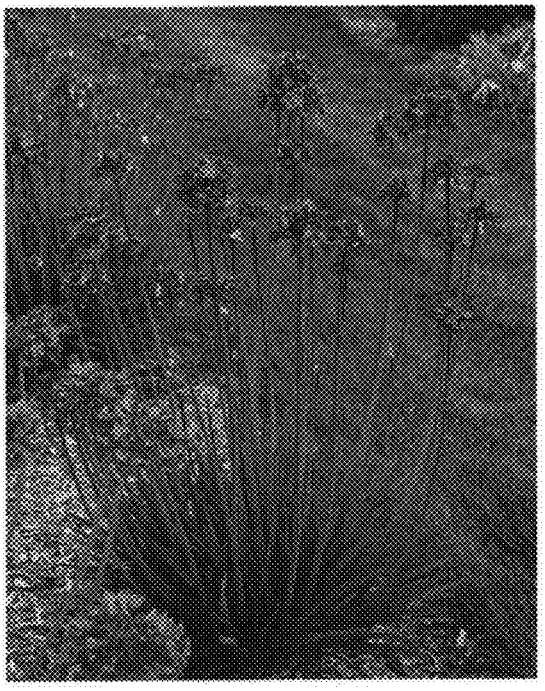
FIG. 1 shows an eight-year-old plant in peak flower during mid-summer in a full-sun trial garden in Zeeland, Mich.
Figure 2:
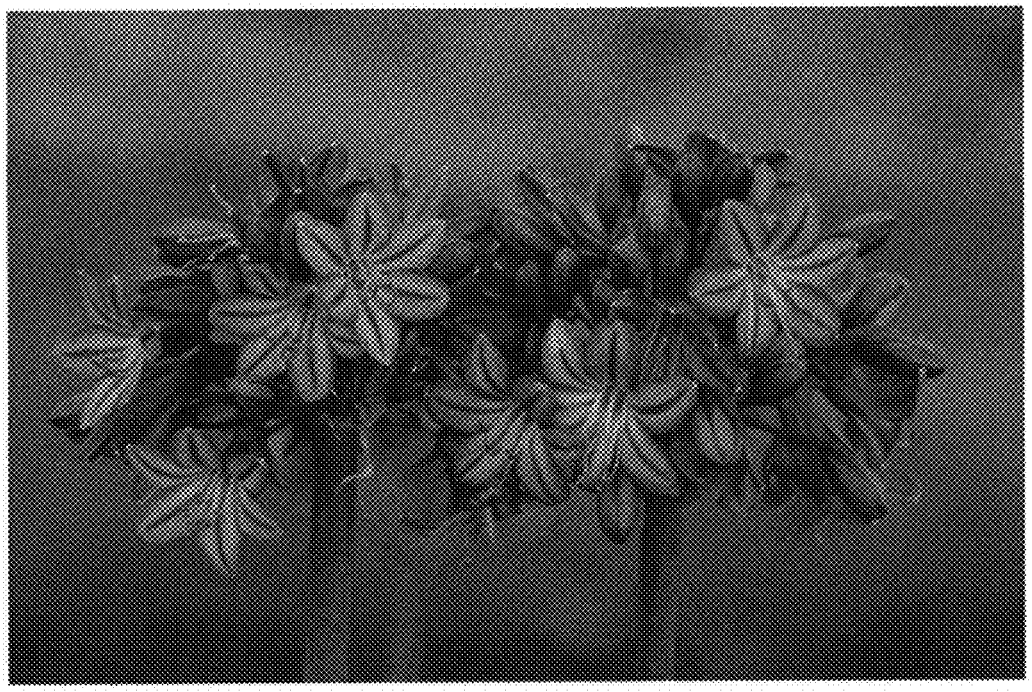
FIG. 2 shows a close-up of the flower and buds.

The following descriptions and color references are based on the 2015 edition of The Royal Horticultural Society Colour Chart except where common dictionary terms are used. The new plant, *Agapanthus* 'Galaxy Blue', has not been observed under all possible environments. The phenotype may vary slightly with different environmental conditions, such as temperature, light, fertility, moisture and maturity levels, but without any change in the genotype. The following observations and size descriptions are of an eight-year-old plant in a sunny research garden bed in Zeeland, Mich. with and supplemental water and fertilizer.

Botanical classification: *Agapanthus praecox* (L.) hybrid;

Parentage: Female (seed) parent is *A. campanulatus* subspecies *patens* 'Mooreanus'; male (pollen) is 'Prolific Blue';

Propagation: Division of the rhizome and shoot tip tissue culture;

Growth rate: Moderate;

Crop time: About 12 to 15 weeks to flower starting in spring in a 3.8 liter container from vernalized one-year-old plant;

Rooting habit: Primary roots thick and fleshy, secondary roots fibrous;

Root color: Nearest RHS 159C depending on soil type;

Plant shape and habit: Winter-hardy herbaceous perennial with pseudo-umbel inflorescence; about 50 flowering stems surrounded by acaulescent foliage forming a dense mound;

Plant size: Foliage height about 32.0 cm tall from soil line to the top of the leaves, about 100.0 cm tall to highest inflorescence and about 80.0 cm wide at the widest point at the top of the inflorescences;

Leaves: Linear; acaulescent; bi-ranked; entire; glabrous and glaucous both abaxial and adaxial; sessile; apex acute, base sheathing scape; to about 32.5 cm long and 17.0 mm across, average about 30.0 cm long and about 16.0 mm across; about 12 per division; attitude upright becoming outright and arching;

Leaf color: Abaxial and adaxial base nearest RHS 144D; mature and young adaxial and abaxial nearest RHS 137A;

Veins: Parallel; abaxial midrib about 2.0 mm across and color same as surrounding leaf tissue;

Inflorescence: Pseudo-umbel initially sheathed in two bracts;

Bracts: Deltoid; dehiscent; acuminate apex; truncate base; scarious; to about 12.0 mm across near middle and 34.0 mm long;

Bract color: Variable; nearest RHS 165D and RHS 165B;

Flowers: Funnelform; single, with two sets of three tepals; about 30 to 50 per scape; upward and outwardly facing; about 30.0 mm across and 22.0 mm deep; individually lasting for about four to five days, individual inflorescence lasting about two weeks; flowers remain effective from late-July repeating into mid-September for approximately eight weeks in Zeeland, Mich.;

Flower fragrance: None detected;

Buds one to two days prior to opening: Ellipsoidal with rounded apex and base; about 16.0 mm long and about 6.0 mm in diameter at widest point with near apex;

Bud color one day from opening: Apical and along tepal margins nearest RHS 94A, lighter proximally nearest RHS 92B toward middle with base nearest portions of RHS 92C and RHS 145D;

Tepals: 2 sets of 3; both sets open to almost flat face; identical in coloration;

Inner tepals: Glabrous; obtuse; rounded apex; base attenuate, fused in proximal 8.0 mm; margin micro-erose; width at base about 2.0 mm; about 10.0 mm across at widest point and about 22.0 mm long;

Outer tepals: Glabrous; obtuse; rounded apex; base attenuate, fused in proximal 8.0 mm; margin entire; width at base about 2.0 mm; about 6.0 mm across at widest point and about 22.0 mm long;

Tepal color adaxial: Distally between RHS 94B and RHS 96B, with a midrib of between RHS 96A and RHS 96B and base lighter than RHS 97D;

Tepal color abaxial: Distally nearest RHS 94B; gradually lightening to lighter than RHS 97D at base;

Pedicel: Cylindrical; average about 30.0 mm long and 1.0 mm diameter; upright to outright;

Pedicel color: Nearest RHS 146B blushed with nearest RHS 187A;

Peduncle: Becoming cylindrical in maturity; usually one per division; erect to about 9.0 mm diameter at base, average 96.0 cm tall; extending above foliage;

Peduncle color: Between RHS 146D and RHS 144A proximally and strongly maculate distally to nearest RHS N187A;

Gynoecium: Single; tricarpelled; about 20.0 mm long;

*Style*.—Single, about 11.0 mm long, 0.5 mm diameter; color nearest RHS NN155D.

*Stigma*.—About 0.3 mm across; color nearest RHS NN155D.

*Ovary*.—Superior; ellipsoidal; about 8.0 mm long and 3.0 mm diameter near middle with an acute apex and truncate base; color nearest RHS 145C.

Androecium: Six;

*Filaments*.—Six; adnate to inner corona in proximal 6.0 mm and free in distal 10.0 mm; about 0.5 mm in diameter; arcuate slightly upward; color nearest RHS 92D.

*Anthers*.—Oblong; basifixed, longitudinal; about 3.0 mm long and 1.0 mm wide; color closest to RHS 4C.

*Pollen*.—Color nearest RHS 11B.

Fruit: Oblong ellipsoidal; non-fleshy, dehiscent, tri-loculicidal capsule with three distinct lobes; about 20.0 mm long and 9.0 mm in across; color while maturing nearest RHS N144D and at dehiscence variable between RHS 164D and RHS 165A;

Seed: Up to about 30 per capsule; flattened single wing with embryo situated near one end; about 7.0 mm long, about 3.5 mm wide and about 1.0 mm thick at embryo; color nearest RHS 202A;

Disease and pest resistance and tolerance: 'Galaxy Blue' shows typical Lily of the Nile resistant to deer and rabbits but has not shown resistance to diseases and pests beyond that common for Lily of the Nile plants. The plant grows best and shows best coloration with plenty of moisture, adequate drainage, but is able to tolerate some drought when mature and direct sun without leaf bum when provided sufficient water.

Hardiness at least from USDA zone 6 through 11. The new plant is useful for landscaping en masse, as a single specimen or small groups, as a container plant or as a cut flower.

The invention claimed is:

1. A new and distinct ornamental plant cultivar named *Agapanthus* 'Galaxy Blue' as herein described and illustrated.

* * * * *